(12) United States Patent
Didur (10) Patent No.: US 9,546,777 B2
(45) Date of Patent: Jan. 17, 2017

(54) ULTRAVIOLET GEMSTONE DISPLAY BOX

(71) Applicant: FINESSE DIAMOND CORP., New York, NY (US)

(72) Inventor: David F. Didur, Ontario (CA)

(73) Assignee: FINESSE DIAMOND CORP, New York, NY (US)

( * ) Notice: Subject to any disclaimer, the term of this patent is extended or adjusted under 35 U.S.C. 154(b) by 0 days.

(21) Appl. No.: 14/991,214

(22) Filed: Jan. 8, 2016

(65) Prior Publication Data

US 2016/0178168 A1    Jun. 23, 2016

Related U.S. Application Data

(63) Continuation-in-part of application No. 13/943,250, filed on Jul. 16, 2013, now abandoned.

(51) Int. Cl.
| | | |
|---|---|---|
| *F21V 19/00* | (2006.01) | |
| *F21V 23/04* | (2006.01) | |
| *F21L 4/00* | (2006.01) | |
| *F21V 5/04* | (2006.01) | |
| *B65D 6/02* | (2006.01) | |

(Continued)

(52) U.S. Cl.
CPC ............ *F21V 19/003* (2013.01); *A45C 11/16* (2013.01); *A47F 7/03* (2013.01); *A47F 11/10* (2013.01); *B65D 9/06* (2013.01); *F21L 4/00* (2013.01); *F21V 5/04* (2013.01); *F21V 23/04* (2013.01);

(Continued)

(58) Field of Classification Search
CPC .......... F21V 19/003; F21V 5/04; F21V 23/04; A45C 11/16; A47F 7/03; A47F 11/10; B65D 9/06; F21L 4/00; F21W 2131/405; G01N 21/87; F21Y 2115/00; F21Y 2101/00
See application file for complete search history.

(56) References Cited

U.S. PATENT DOCUMENTS 3,937,320 A * 2/1976 Chao ...................... A45C 15/06
                                                          206/216
3,944,368 A    3/1976 Beesley
(Continued)

OTHER PUBLICATIONS

T. M. Moses, et al., "A Contribution to Understanding the Effect of Blue Fluorescence on the Appearance of Diamonds," Gems & Gemology, Winter 1997, pp. 244-259.

(Continued)

*Primary Examiner* — Bao Q Truong
(74) *Attorney, Agent, or Firm* — Banner & Witcoff, Ltd.

(57) ABSTRACT

A display box displays the fluorescence of a gemstone having naturally occurring phosphors. The box has a top portion hinged with a bottom portion. A compact ultraviolet LED assembly is mounted at a mounting angle in the insert in a cavity of the top portion. The LED assembly has: an LED circuit; a 3 watt 365 nm ultraviolet LED diode disposed on the LED circuit; and an optical collimator having a parabolic lens to focus the emitted LED radiation to a less than 15° spread. A compact battery for powering the LED assembly is provided in a recess of the bottom portion. A central holder/deck holds the gemstone in a direct path of the emitted collimated LED radiation of the LED assembly. In operation, the gemstone seated in the central holder/deck emits a corona of strong visible fluorescence while the ultraviolet radiation and the LED assembly are not seen.

10 Claims, 9 Drawing Sheets
(2 of 9 Drawing Sheet(s) Filed in Color)

(51) Int. Cl.
  *A45C 11/16* (2006.01)
  *A47F 7/03* (2006.01)
  *A47F 11/10* (2006.01)
  *F21W 131/405* (2006.01)
  *G01N 21/87* (2006.01)
  *F21Y 101/00* (2016.01)

(52) U.S. Cl.
  CPC ..... *F21W 2131/405* (2013.01); *F21Y 2101/00* (2013.01); *G01N 21/87* (2013.01)

(56) References Cited

U.S. PATENT DOCUMENTS

| | | | |
|---|---|---|---|
| 3,984,674 A | 10/1976 | Guetta | |
| 5,329,433 A * | 7/1994 | Geeting | A45C 11/16 16/223 |
| 6,405,858 B1 * | 6/2002 | Gagliardi | A45C 11/16 206/566 |
| 6,433,483 B1 | 8/2002 | Michael et al. | |
| 6,776,281 B2 | 8/2004 | Ovadia | |
| 6,844,686 B1 * | 1/2005 | Schneck | A45C 11/16 315/185 S |
| 7,325,940 B2 * | 2/2008 | Cea | A45C 11/16 206/566 |
| 8,403,517 B1 | 3/2013 | Cox et al. | |
| 8,878,145 B1 | 11/2014 | Liu | |
| 2003/0167795 A1 | 9/2003 | Metcalfe et al. | |
| 2004/0141320 A1 | 7/2004 | Bock et al. | |
| 2004/0213088 A1 | 10/2004 | Fuwausa | |
| 2007/0165408 A1 | 7/2007 | Li | |
| 2015/0021497 A1 * | 1/2015 | Didur | A47F 7/03 250/461.1 |

OTHER PUBLICATIONS

Diamond Fluorescence [online] [retrieved Jan. 12, 2016]. Retrieved from Internet <URL:http://www.lumeradiamonds.com/diamond-education/diamond-fluorescence>; 4 color sheets.

Understanding Diamond Fluorescence [online] [retrieved Jan. 12, 2016]. Retrieved from Internet <URL:http://4csblog.gia.edu/2012/understanding-diamond-fluorescence>; 8 color sheets.

GEM DiamondLite, [online] [retrieved Jan. 12, 2016]. Retrieved from Internet <URL:http://anchorcertgemlab.com/about-us/diamond-lite>; 2 color sheets.

System Eickhorst UV-Colorscope EC, [online] [retrieved Jan. 12, 2016] Retrieved from Internet <URL:http://www.eickhorst.com/en/gemmological-instruments/uv-lamps/uv-colorscope/features/>; 2 color sheets.

\* cited by examiner

ULTRAVIOLET GEMSTONE DISPLAY BOX

CROSS REFERENCE TO RELATED APPLICATIONS

The present application is a continuation-in-part of U.S. application Ser. No. 13/943,250 filed on Jul. 16, 2013, the contents therein are incorporated by reference.

FIELD OF THE INVENTION

Aspects relate to an apparatus for providing high-powered, focused ultraviolet radiation to a gemstone having naturally occurring phosphors to display the fluorescence of the gemstone in a striking and eye-catching fashion.

BACKGROUND OF THE INVENTION

The existence of phosphors in certain gemstones (e.g. diamonds) has been known to jewellers and gemologists for many years. In the case of diamonds, phosphors may be present in the form of impurity atoms of nitrogen, hydrogen and boron. These phosphors are largely undetectable in natural light conditions. However, under ultraviolet light, the phosphors may fluoresce in shades of orange, blue, yellow or green. Fluorescence refers to the property of a substance to emit light through absorbed UV radiation, while exposed to the source of the UV radiation. The Gemological Institute of America has estimated that approximately 25% to 35% of diamonds have some degree of fluorescence.

Figure 1:
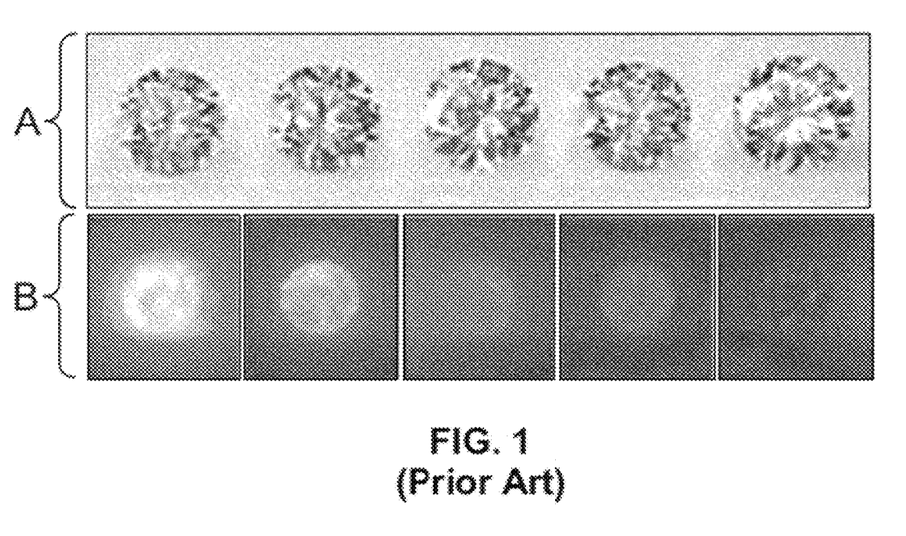
FIG. 1 is a prior art array of a set of standard diamonds exhibiting different degrees of natural phosphors. The second half of the figure shows the diamonds fluoresced under ultraviolet light.

As seen in FIG. 1, diamonds containing phosphors in different concentrations may be virtually indistinguishable from each other in natural light (A), but become differentially fluoresced when exposed to ultraviolet radiation (B). The fluorescence appears as the emitting of lumens directly from the gemstone.

When present in strong concentrations, the presence of these phosphors has been associated with flawed or lower quality stones. Thus, fluorescence has been used as a grading and descriptive tool by jewellers and gemologists. Ultraviolet inspection lights are typically used under laboratory conditions where outside light is blocked out. Such ultraviolet lights are not used in the presence of customers or in a store setting with typically bright ambient lighting. Further, the perceived negative value of the fluorescent stones has meant that jewellers have sought to hide this feature from, or deemphasize it, to customers. Stones with Medium Blue or Strong Blue or Very Strong Blue fluorescence grades trade at very significant discounts, sometimes as much as thirty to forty percent.

This effect has not been used in a display context where the phosphor containing properties of gemstones were particularly highlighted or promoted.

Typical jewelry boxes and displays highlight the beauty of a gemstone or piece of jewelry by showcasing it in ambient light, or with display lighting reflected off the gemstone or jewelry piece. However, although existing boxes may serve to provide a glamorized context or backdrop for a piece of jewelry, they operate simply as static holders that themselves do nothing to actively promote or stimulate the jewelry piece to show itself to the buyer or recipient.

It would be desirable to provide a display box for actively displaying fluorescence of a gemstone having naturally occurring phosphors in order to allow consumers to see the rarity and uniqueness of such stones that were typically only "seen" in this way by jewellers and gemologists.

SUMMARY OF THE INVENTION

Aspects pertains to a display box is provided for displaying fluorescence of a gemstone having naturally occurring phosphors. The box has a top portion having an interior cavity. An insert is provided mounted in the interior cavity of the top portion. A compact ultraviolet LED assembly is mounted at a mounting angle in the insert. The LED assembly has: an LED circuit, a 3 watt 365 nm ultraviolet LED diode disposed on the LED circuit, and an optical collimator having a parabolic lens to focus the emitted LED radiation to a less than 15° spread. A bottom portion of the box is provided in hinged relation with the top portion. The bottom portion has a recess for containing a compact battery for powering the LED assembly. A central holder/deck is positioned in the bottom portion over the battery for retaining the gemstone so that the gemstone is retained in a direct path of the emitted collimated LED radiation of the LED assembly. The box is structured such that in operation the gemstone seated in the central holder/deck emits a corona of strong visible fluorescence while the ultraviolet radiation and the LED assembly are not seen.

Preferably, the compact battery is a lithium ion cell. More preferably, the compact battery is a lithium ion cell having an output of at least 1000 milliampere hours (mAh).

Preferably, the mounting angle of the LED assembly is approximately 60°. Preferably, the position, size and mounting angle of the LED assembly are selected to avoid contact between the LED assembly and the gemstone when the box is closed.

The optical collimator is preferably selected to collimate the emitted radiation to have (no more than) an 8-10° spread. This focus of the emitted radiation is used to strike the gemstone as directly as possible without a dilution of spectral distribution. Further, the parabolic lens shape may be selected to avoid the emitted ultraviolet radiation striking surfaces of the box other than the gemstone.

A programmable chipset is preferably used in communication with the LED assembly for thermal management.

A switch, such as a pressure switch, may be provided on one or the other of the top and bottom portions, in communication with the LED assembly, for turning off power to the LED assembly when the box is closed. A separate cycling switch may also be provided in communication with the LED assembly for producing display effects while the box is open.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

The present display box operates to display the fluorescence of a gemstone having naturally occurring phosphors. The structure of the box uses a hidden high-intensity LED assembly and the (naturally invisible) emitted radiation of an ultraviolet diode, which is focussed in a collimated form, so that the gemstone in the box can present itself in a unique and striking form. While under the effect of the ultraviolet radiation, the gem itself emits visible illumination through its fluorescence. When the radiation source is shut off, the effect ceases.

This allows the display box to provide a new experience to jewelry buyers and recipients. By effect of the display box, but without readily visible sources, when the box opens, the gemstone appears spontaneously to "pop" to the observer's attention.

Figure 2A:
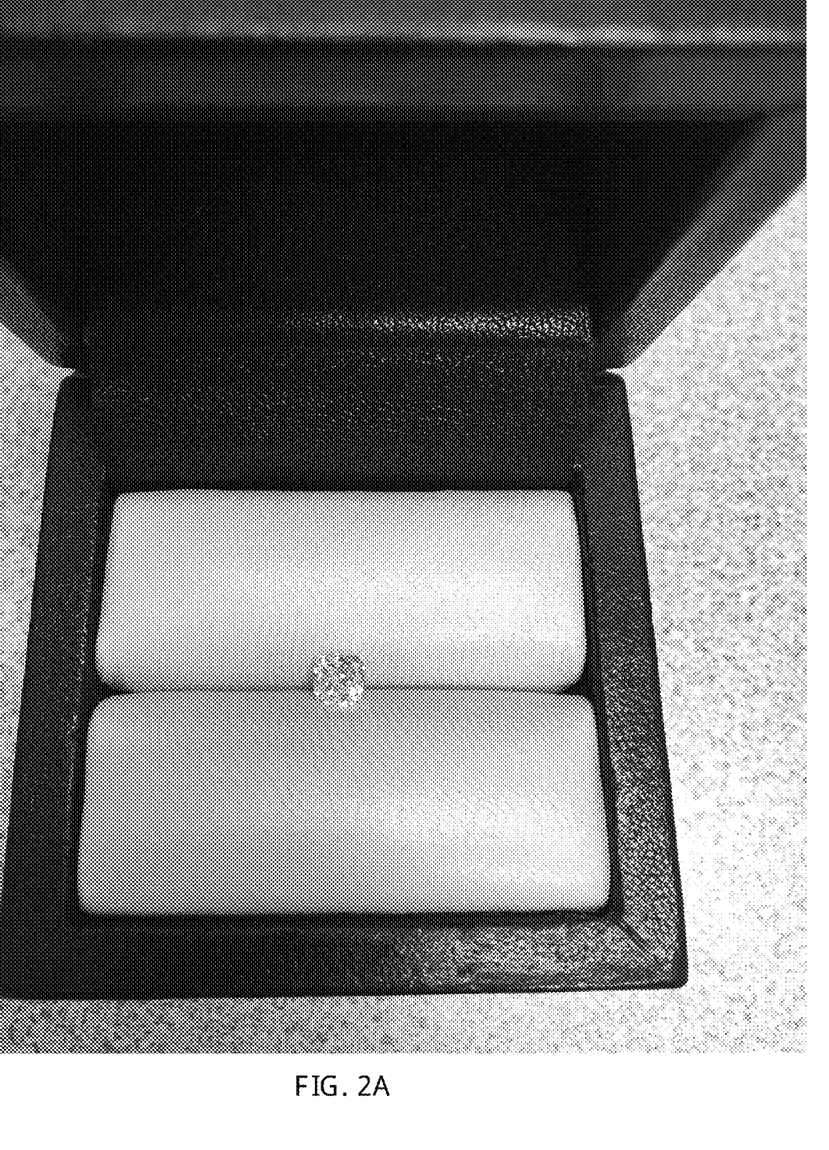
FIGS. 2A and 2B are two photographic views of an embodiment of the present display box (open state) showing a jewelry piece in natural light (FIG. 2A) and fluoresced by the hidden UV LED assembly of the display box in dimmed atmospheric lighting (FIG. 2B).
Figure 2B:
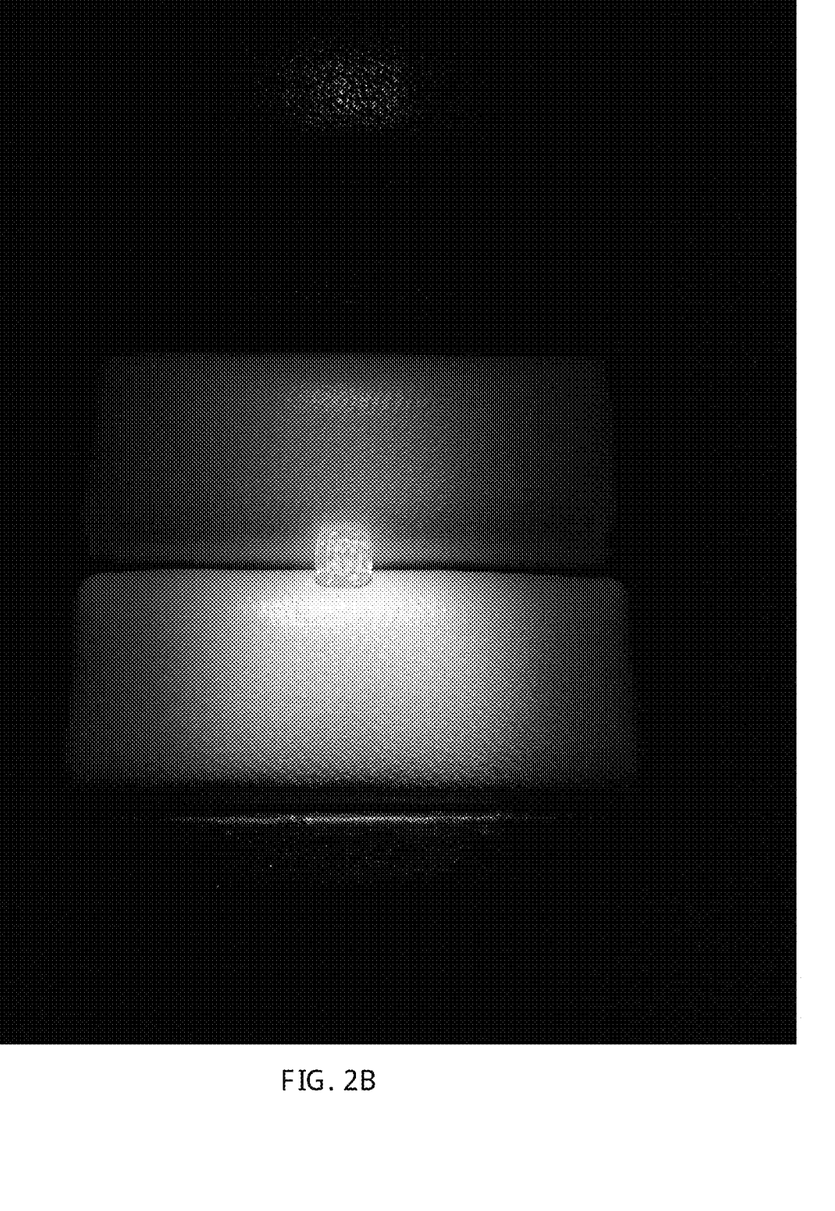

FIGS. 2A and 2B are two photographic views of an embodiment of the present display box (open state) showing a jewelry piece. In FIG. 2A, the jewelry piece (here, a diamond) is in natural light (UV LED turned off). In FIG. 2B, the jewelry piece is shown fluoresced by the hidden UV LED assembly of the display box in dimmed atmospheric lighting. As one can see in these "before" and "after" photographs, the spectral effect of the fluoresced stone under the effect of the UV radiation emitted from the hidden LED in the box is quite intense, and even more striking under dimmed atmospheric lighting. The stone itself, in a corona of light, appears to hover apart from its mounting and the box holder.

This effect stands in contrast to even the inspection-grade ultraviolet lights used for diamond grading as seen in the standard diamonds shown in FIG. 1 (prior art). Particular care has been taken in the present invention to exaggerate and enhance the fluorescence of the stone by the use of high-intensity (3 W) ultraviolet radiation at a particular long-wave wavelength (365 nm) in a tightly collimated form for targeted energizing of the gemstone.

Let us turn to how these effects are achieved by beginning our examination of the structure of the present box.

Figure 3:
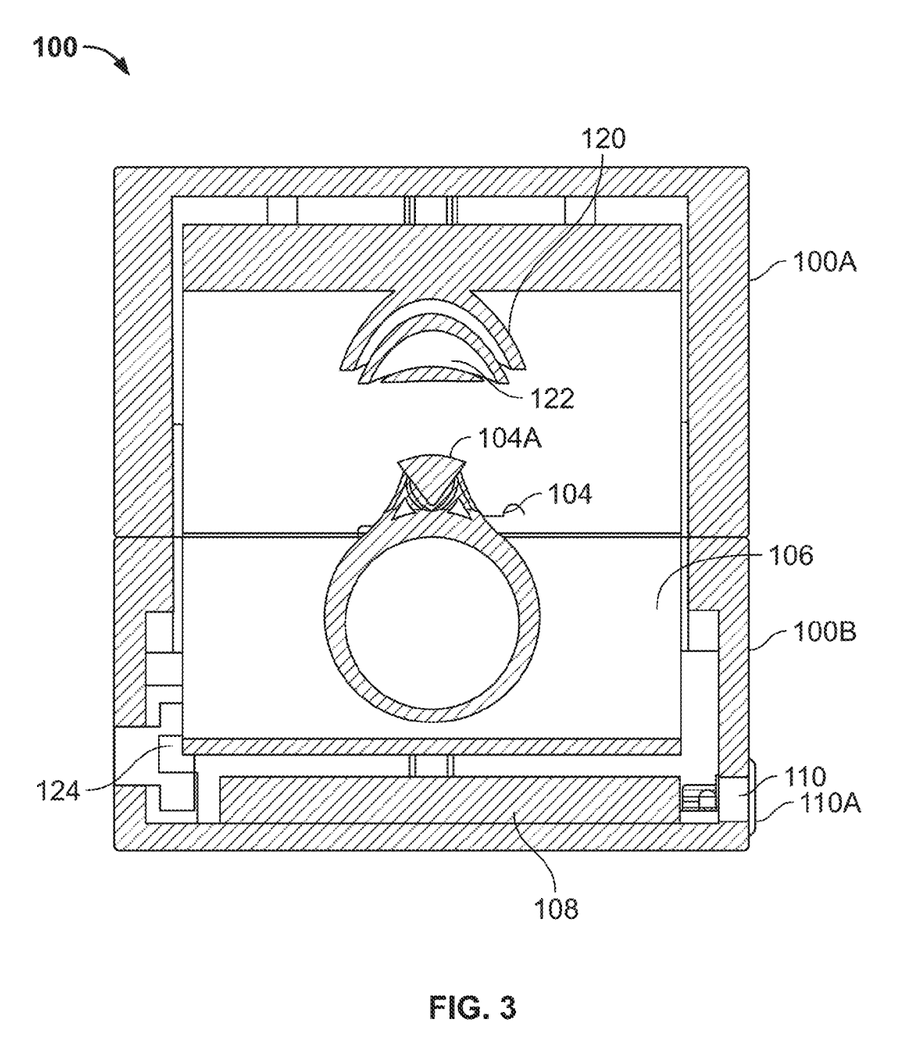
FIG. 3 is a front sectional view of an embodiment of the present display box in a closed state.
Figure 8:
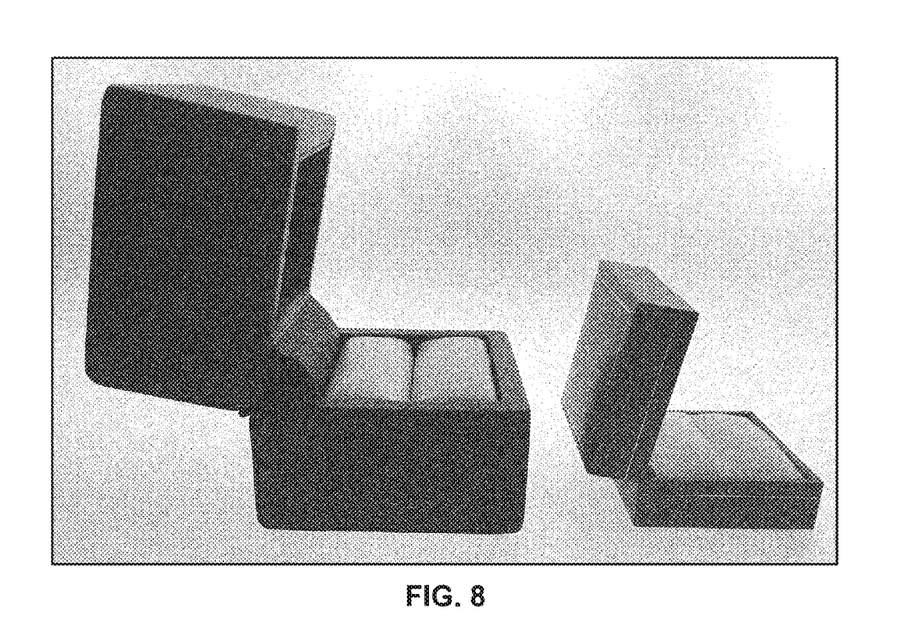
FIGS. 8 and 9 are two photographic views of an embodiment of the present display box beside a standard jewelry box for scale comparison with FIG. 8 being a closed state and FIG. 9 being an open state.
Figure 9:
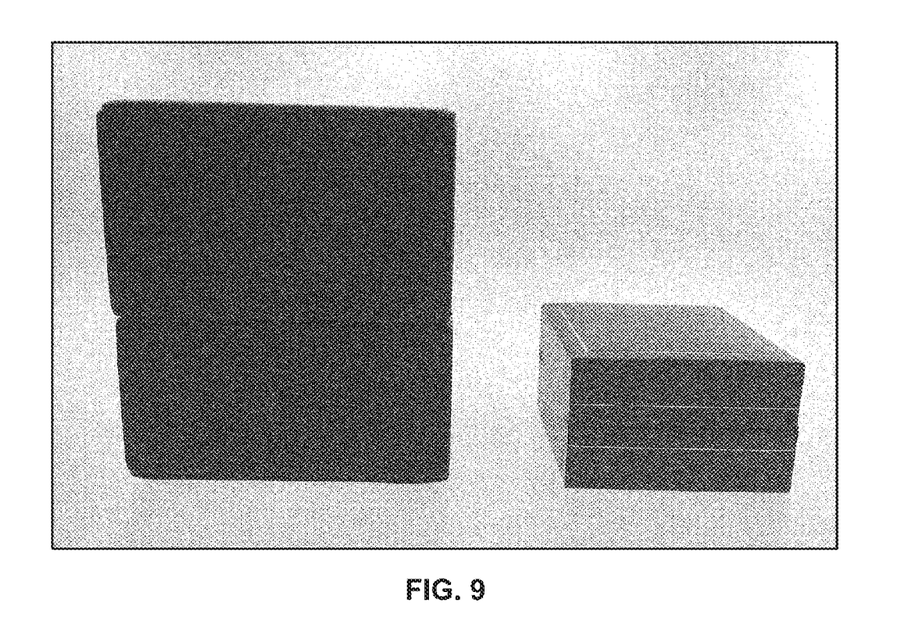

A simple illustration of the box 100 is perhaps seen in FIG. 3, which shows a front sectional view in a closed state. As shown, the box 100 has two general parts—a top portion 100A, and a bottom portion 100B. The box overall may be approximately 2-3 inches square, with a height of approximately 3-4 inches. The top and bottom portions 100A, 100B may be taller/deeper than the dimensions of a typical jewelry box in order to accommodate the recessed components of the LED assembly, battery and electronics. The relatively deeper clamshell lid, and relatively limited hinge angle of the box (preferably less than 90°) is also engineered to keep out ambient light (unlike standard jewelry boxes which typically open wider to permit more ambient light or display lighting to enter). The differences in dimensions compared to a standard jewelry box are illustrated in FIGS. 8 and 9.

Importantly, as can clearly be seen in FIG. 3, the jewelry piece 104 with its gemstone 104A is positionable in a deck/insert 106 in the bottom portion 100B such that the jewelry piece does not contact the LED assembly 122 mounted in an insert 120 in the top portion 100A when the two halves are closed.

Figure 4:
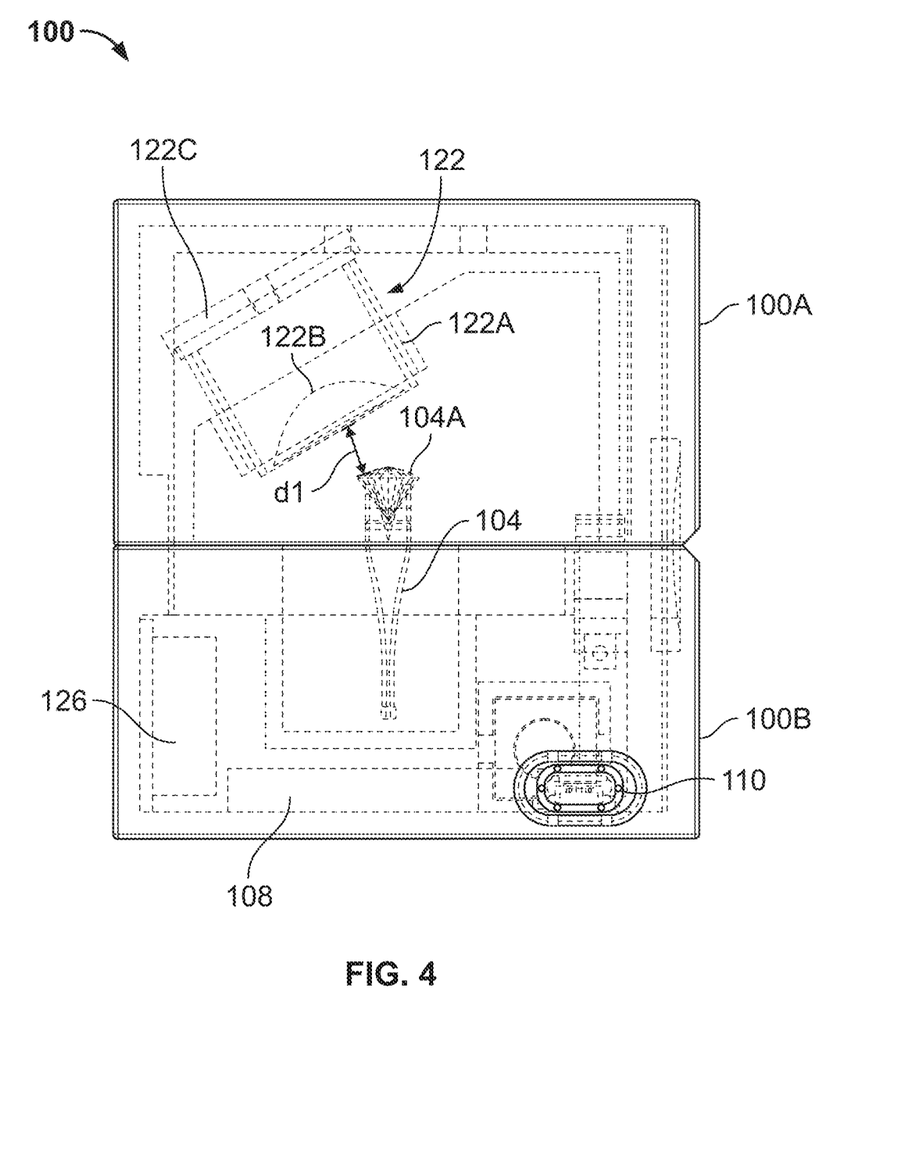
FIG. 4 is right side sectional view of the display box (closed state).

This clearance is also seen in FIG. 4 (distance d1 between the top edge of jewelry piece 104 to the bottom face of the LED assembly 122—typically less than 0.5 inches). The mounting angle of the LED assembly 122 (circumscribed by the insert 120) also contributes to the clearance between the jewelry piece 104 and the LED assembly 122. The LED assembly 122 as a whole is mounted at an angle of approximately 60° relative to the axis of the box lid.

The LED assembly 122 includes an LED circuit 122C. This circuit 122C includes a light-emitting diode (not specifically numbered) for emitting ultraviolet radiation, most preferably at the specific ultraviolet wavelength of 365 nanometers (nm). The diode is a high-powered diode at 3 watts. The power is provided by a compact battery, preferably a lithium ion cell of at least approximately 1000 mAh. The battery is wired to the LED circuit through hidden wire raceways in the walls of the bottom and top portions of the box (not specifically numbered).

Figure 5:
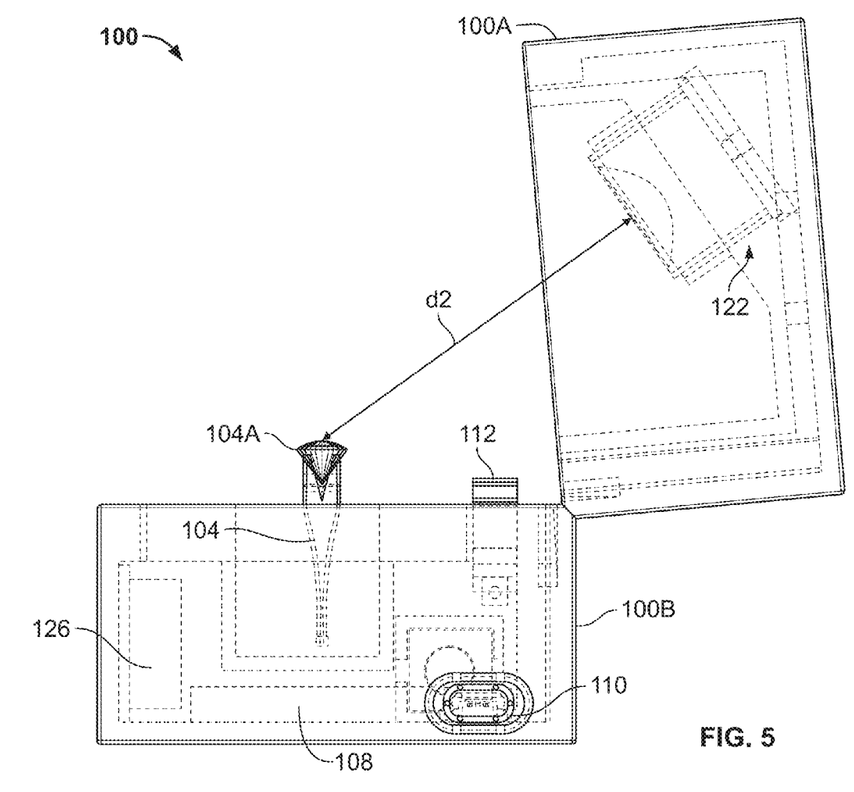
FIG. 5 is a right side sectional view of the display box (open state).

Attached to the circuit 122C, and secured to form an overall compact assembly 122, is an optical collimator 122A. Using a parabolic lens 122B, the optical collimator receives and narrows the UV radiation beam emitted by the UV LED. The path of this collimated beam is best seen in FIG. 5. The configuration of the box means that the distance (d2) between the LED assembly 122 and the gemstone 104A is relatively small (approximately 2-3 inches when the box is open). This short distance allows for minimal energy dissipation. In this way, the jewelry box form factor also provides a consistent short-range path from emitter to target, unlike even the typical "inspection" conditions, where the typically-desk-mounted UV source may be positioned 12-18 inches or more from the target stone. UV decays over distance leading to a less impressive resulting fluorescent effect.

In the energized state, the LED emits a beam of UV radiation that is collimated and focussed (angle a of less than 15°, and more preferably no more than 8-10°) to directly strike the gemstone retained in the deck/insert 106 of the bottom portion 100B. The angle and the particular focus on the gemstone area also allows the emitted UV to strike primarily or only the intended target (the stone) avoiding surfaces of the box. UV radiation can have a destructive effect over time on many materials.

Figure 5A:
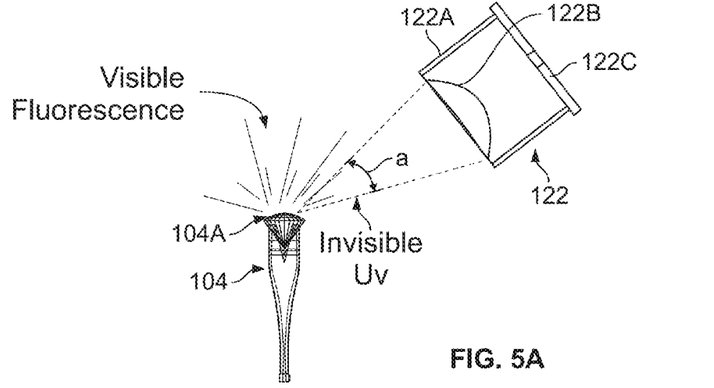
FIG. 5A is a detail view of the LED assembly and jewelry piece showing angle of collimated UV radiation beam (invisible) and visible fluorescence of the gemstone.

The invisible UV energy is in watts (here, preferably at least 3 watts), a radiometric output (i.e. the intensity of power output). The energy becomes visible fluorescence emitted by the gemstone 104A, as conceptually illustrated in FIG. 5A. The fluorescent light emitted by the gemstone is a form of photometric output, which is typically measured in lumens depending on how bright the light appears to the human observer.

When using high-intensity ultraviolet diodes in the tight space (small form factor) of a jewelry box, there is a concern for thermal management. UV LEDs create more heat than LEDs of other wavelengths. Accordingly, a passive heat sink may be provided in direct physical communication with the LED circuit (not shown) to dissipate heat from the diode. Alternatively, a programmable chipset 126 may be used to manage temperature through a feedback process of converting heat as it is created to more emitted energy. The chipset is preferably stored in the bottom portion 100B of the box 100 in wired communication with the LED assembly 122 through hidden wire raceways.

Figure 6:
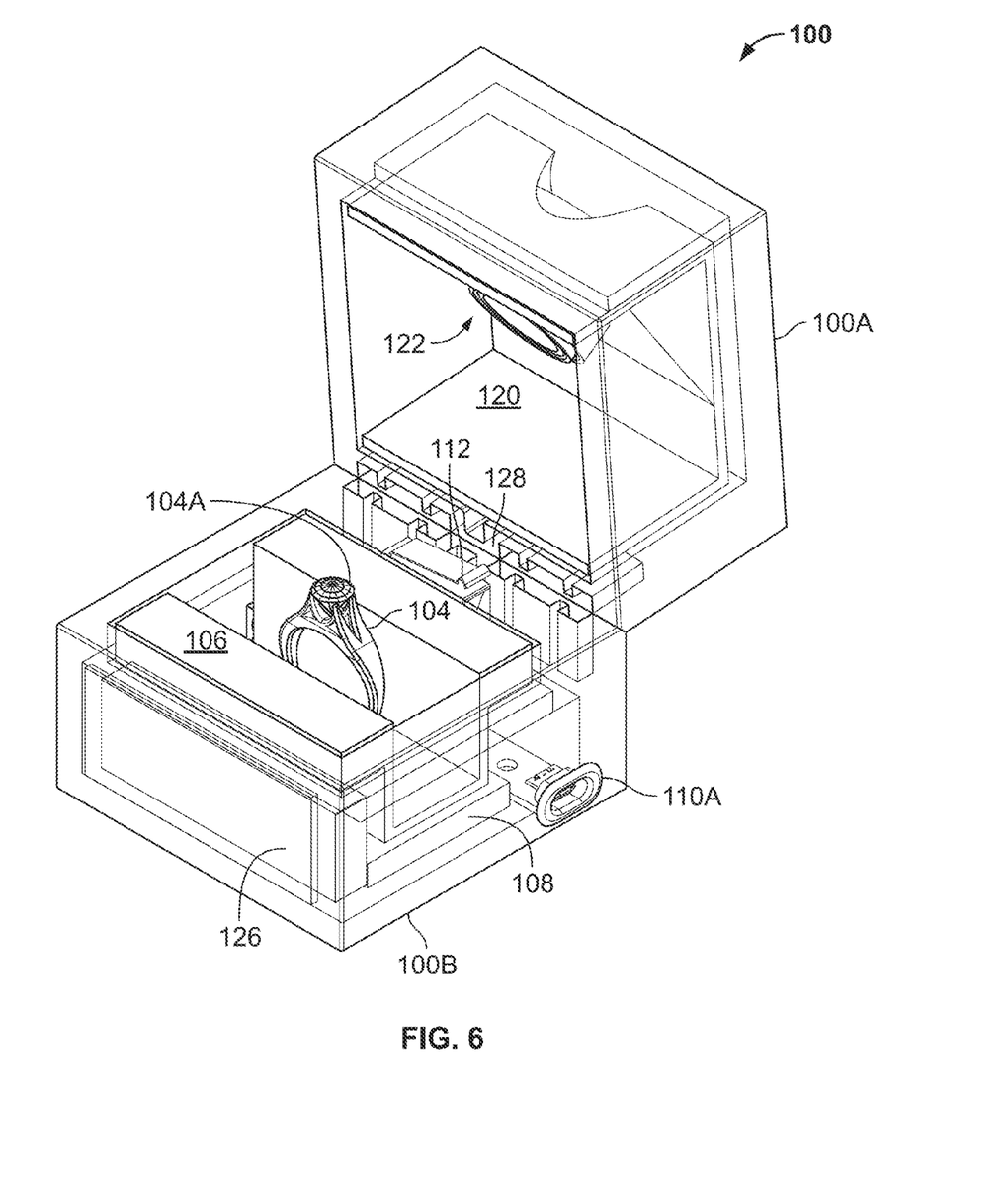
FIG. 6 is a perspective view of the display box (open state), angled slightly to show the otherwise hidden LED assembly.

FIG. 6 is a perspective view of the display box (open state), angled slightly to show the otherwise hidden LED assembly mounted in insert 120. (The "hiddenness" is best observed in FIG. 2A.) Jewelry piece 104 with gemstone 104A is mounted in deck/insert 106. The battery 108 and programmable chipset are hidden below deck/insert 106.

Figure 7:
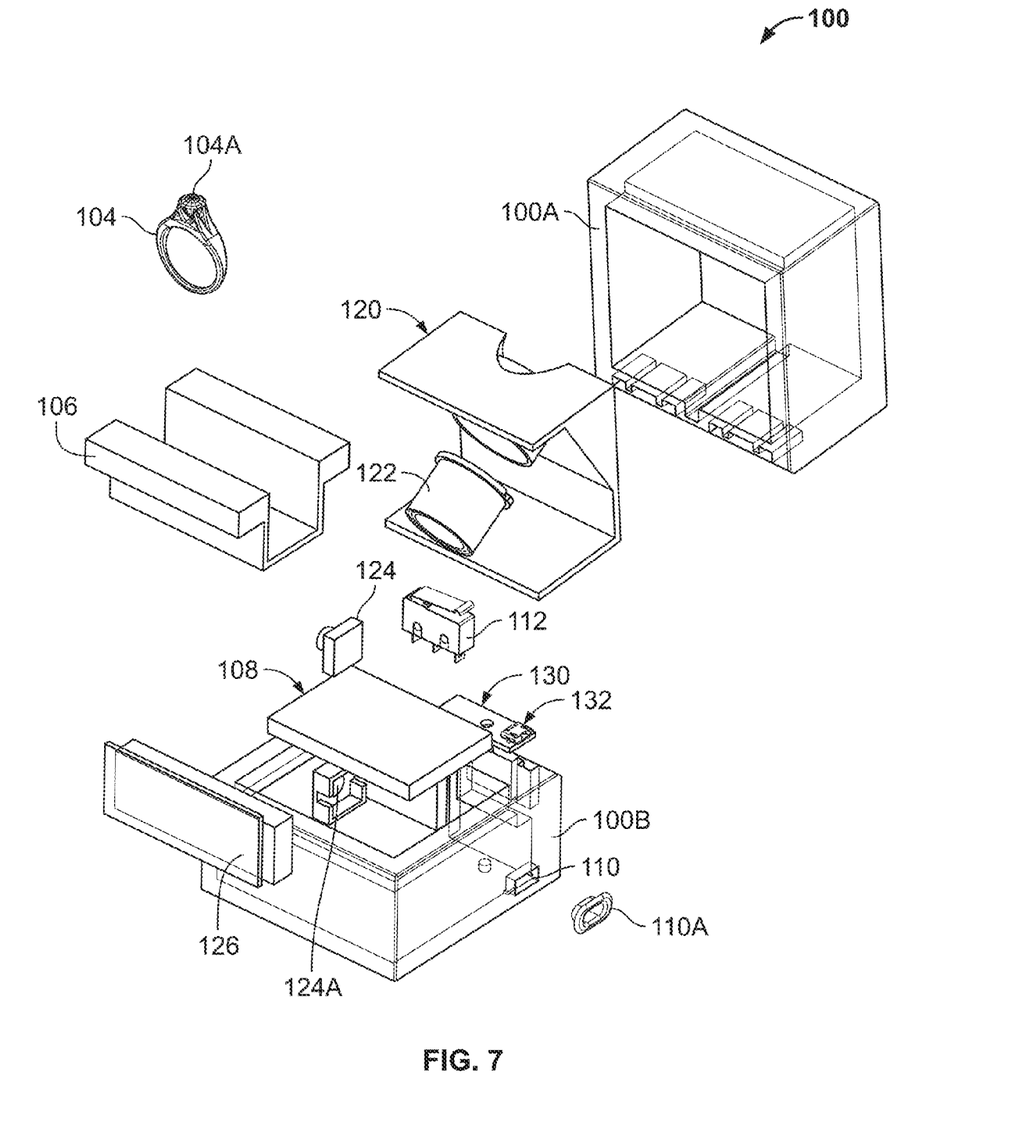
FIG. 7 is an exploded component view of the display box.

FIG. 6 also illustrates the box switch (here pressure switch 112) which when contacted by surface 128 of top portion 100A, shuts the power circuit from the battery 108 to the LED assembly 122. Although shown open, in a commercial embodiment, this may be covered over by a soft textile or other padded covering (see FIGS. 2A, 2B for an example) to disguise the switch. This switch may be in communication with a circuit board 130 and USB molex 132 as shown in FIG. 7. The molex serves to convert power input from a USB source (5-7 volt) through recharge port 110 (surrounded by grommet 110A) to recharge battery 108 and may be used to simultaneously power the LED assembly while recharging. Other forms of rechargeable power may be provided (e.g. AC). In continuous operation, applicants have found that a battery of the type used here (1000 mAh lithium ion) lasts about 10-12 hours on a single charge.

Optionally, a cyclic switch 124 may also be provided (accessible through access port 124A) which communicates with the programmable chipset to allow display effects (e.g. timed on-off sequences, shutdown after a period of time, or graduated intensity effects) to be toggled while the box is open. That is, the UV LED (which is default "on" (i.e. radiation emitting) when the box is open) can be otherwise directed by the programmable chipset 126 to perform other sequences. This is the same programmable chipset 126 used for thermal management as described above.

Although this present invention has been disclosed with reference to specific forms and embodiments, it will be evident that a great number of variations may be made without departing from the spirit and scope of the present invention. For example, equivalent elements may be substituted for those specifically disclosed and certain features of the present invention may be used independently of other features—all without departing from the present invention as defined in the appended claims.

What is claimed is:

1. A display box for displaying fluorescence of a gemstone having naturally occurring phosphors, comprising:
a top portion having an interior cavity;
an insert mounted in the interior cavity of the top portion;
a compact ultraviolet LED assembly mounted at a mounting angle in the insert, the LED assembly having:
an LED circuit;
a 3 watt 365 nm ultraviolet LED diode disposed on the LED circuit;
an optical collimator having a parabolic lens to focus the emitted LED radiation to a less than 15° spread;
a bottom portion in hinged relation with the top portion, and having a recess for containing a compact battery for powering the LED assembly; and
a central holder/deck positioned in the bottom portion over the battery for retaining the gemstone so that the gemstone is retained in a direct path of the emitted collimated LED radiation of the LED assembly;
such that the gemstone seated in the central holder/deck emits a corona of strong visible fluorescence while the ultraviolet radiation and the LED assembly are not seen.

2. The display box of claim 1, wherein the compact battery is a lithium ion cell.

3. The display box of claim 2, wherein the lithium ion cell has an output of at least 1000 mAh.

4. The display box of claim 1, wherein the mounting angle of the LED assembly is 60°.

5. The display box of claim 1, wherein the emitted radiation is collimated to have an 8-10° spread.

6. The display box of claim 1, further comprising a programmable chipset in communication with the LED assembly for thermal management.

7. The display box of claim 1, further comprising a pressure switch on one or the other of the top and bottom portions, in communication with the LED assembly for turning off power to the LED assembly when the box is closed.

8. The display box of claim 1, further comprising a cycling switch in communication with the LED assembly for producing display effects while the box is open.

9. The display box of claim 1, wherein the parabolic lens shape is selected to avoid the emitted ultraviolet radiation striking surfaces of the box other than the gemstone.

10. The display box of claim 1, wherein the position, size and mounting angle of the LED assembly are selected to avoid contact between the LED assembly and the gemstone when the box is closed.

* * * * *